United States Patent [19]

(12) United States Patent
Ma et al.

(10) Patent No.: US 12,298,280 B2
(45) Date of Patent: May 13, 2025

(54) METHOD FOR INCREASING NUMBER OF PROTEINS IDENTIFIED BY MASS SPECTROMETRY

(71) Applicant: PROTEINT (TIANJIN) BIOTECHNOLOGY CO., LTD, Tianjin (CN)

(72) Inventors: Congcong Ma, Tianjin (CN); Jin Zhao, Tianjin (CN); Xubo Yuan, Tianjin (CN); Liangyu Chen, Tianjin (CN); Lei Song, Tianjin (CN); Li Ren, Tianjin (CN); Jie Li, Tianjin (CN)

(73) Assignee: PROTEINT (TIANJIN) BIOTECHNOLOGY CO., LTD (CN)

( * ) Notice: Subject to any disclaimer, the term of this patent is extended or adjusted under 35 U.S.C. 154(b) by 0 days.

(21) Appl. No.: 18/691,905

(22) PCT Filed: Oct. 27, 2021

(86) PCT No.: PCT/CN2021/126630
§ 371 (c)(1),
(2) Date: Mar. 14, 2024

(87) PCT Pub. No.: WO2023/040006
PCT Pub. Date: Mar. 23, 2023

(65) Prior Publication Data
US 2024/0264128 A1 Aug. 8, 2024

(30) Foreign Application Priority Data

Sep. 14, 2021 (CN) .......................... 202111076303.8
Oct. 26, 2021 (CN) .......................... 202111243949.0

(51) Int. Cl.
G01N 30/06 (2006.01)
G01N 30/72 (2006.01)
G01N 33/68 (2006.01)

(52) U.S. Cl.
CPC ......... *G01N 30/06* (2013.01); *G01N 30/7233* (2013.01); *G01N 33/6848* (2013.01)

(58) Field of Classification Search
None
See application file for complete search history.

(56) References Cited

FOREIGN PATENT DOCUMENTS

| CN | 1431497 A | 7/2003 |
| CN | 1560625 A | 1/2005 |

(Continued)

OTHER PUBLICATIONS

Klint, D. et al. Conditions for the Adsorption of Proteins on Ultrastable Zeolite Y and Its Use in Protein Purification, Protein Expression and Purification 10, 247-255 (1997) (Year: 1997).*

(Continued)

*Primary Examiner* — Xiaoyun R Xu

(57) ABSTRACT

The present disclosure provides a method for increasing a number of proteins identified, including: S1. adding a binding buffer and an aluminosilicate zeolite to a sample to be tested to obtain a first suspension; S2. incubating the first suspension, subjecting an incubated first suspension to first high-speed centrifugation to obtain a first supernatant and a first precipitate, discarding the first supernatant, and retaining the first precipitate; S3. repeating a process as follows several times: resuspending the first precipitate with a washing buffer to obtain a second suspension, subjecting the second suspension to second high-speed centrifugation to obtain a second supernatant and a second precipitate, discarding the second supernatant, and retaining the second precipitate; and S4. preparing the second precipitate into a protein sample, and subjecting the protein sample to mass spectrometry detection.

6 Claims, 3 Drawing Sheets

(56) References Cited

FOREIGN PATENT DOCUMENTS

| CN | 108333263 A | 7/2018 |
| --- | --- | --- |
| CN | 112710755 A | 4/2021 |
| CN | 111721939 A | 9/2023 |
| WO | 2010102162 A1 | 9/2010 |

OTHER PUBLICATIONS

Choi, D-S, et al. Isolation of Extracellular Vesicles for Proteomic Profiling, Proteomic Profiling: Methods and Protocols, Methods in Molecular Biology, vol. 1295, p. 167-177 (Year: 2015).*

Muller, T. et al. Systematic Evaluation of Protein Reduction and Alkylation Reveals Massive Unspecific Side Effects by Iodine-containing Reagents, Molecular & Cellular Proteomics 16.7, pp. 1173-1187 (Year: 2017).*

Title: Capillary electrophoresis—research on new technologies for mass spectrometry and sample enrichment and their application in proteins Applications in genomics research Author: Wang Xiaoyan University: Fudan University Type: Postdoctoral thesis.

* cited by examiner

METHOD FOR INCREASING NUMBER OF PROTEINS IDENTIFIED BY MASS SPECTROMETRY

CROSS REFERENCE TO RELATED APPLICATION

This application is a national stage entry of International Application No. PCT/CN2021/126630, filed on Oct. 27, 2021, which is based upon and claims foreign priority to Chinese Patent Application No. 202111076303.8, filed on Sep. 14, 2021 and Chinese Patent Application No. 202111243949.0, filed on Oct. 26, 2021, the entire contents of which are incorporated herein by reference.

TECHNICAL FIELD

The present disclosure belongs to the technical field of proteomics, and specifically relates to a method for increasing a number of proteins identified by mass spectrometry using aluminosilicate zeolite.

BACKGROUND

Serum/plasma is a free-flowing fluid in an organism and contains substances released by various tissues and organs of the organism. Thus, serum/plasma has a large amount of potentially-available physiological or pathological information. It is estimated that there are more than 10,000 types of proteins in serum/plasma, but only a small part of these proteins can be detected due to the limitations in current detection and identification techniques. Serum/plasma has dozens of high-abundance proteins accounting for 95% or more of a total serum/plasma protein content, making it difficult to isolate and separate plasma/serum proteins. Currently, when high-abundance proteins are not depleted, only 300 to 400 proteins can be detected by mass spectrometry of protein. When a commercial antibody-based high-abundance protein-depletion kit is used, the number of identified proteins can be increased to 400 to 800.

Zeolites refer to synthetic hydrated aluminosilicates with molecular screening effects. Its general chemical formula is (M'2M)O·Al2O3·xSiO2·yH2O, where M' and M represent monovalent and divalent cations, respectively, such as K+ or Na+ and Ca2+ or Ba2+. The zeolite structurally has many orderly-arranged pores with a uniform pore size. Zeolites with different pore sizes can separate molecules of different sizes and shapes. According to different molecular ratios of SiO2 to Al2O3, zeolites with different pore sizes can be obtained. The zeolites are widely used in organic chemical and petrochemical industries due to their high adsorption capacity, strong selectivity, and high-temperature resistance. The zeolites are also excellent adsorbents for coal gas dehydration. However, there are currently no exploratory studies on the use of the zeolites to deplete high-abundance proteins and peptides and enrich low-abundance proteins and peptides in serum/plasma.

SUMMARY

In view of limitations of the current preparation method of a serum/plasma protein and peptide sample, the present disclosure provides a method for increasing a number of proteins by mass spectrometry using aluminosilicate zeolite. In the present disclosure, an aluminosilicate zeolite and a corresponding binding buffer are used to achieve qualitative and quantitative analysis for serum/plasma proteins and peptides, and can effectively increase a number of identified proteins. In addition, the aluminosilicate zeolite can achieve the enrichment, enzymolysis, and desalination of microsamples at a protein level or a peptide level. The aluminosilicate zeolite can also be used as a solid-phase enrichment carrier in place of the existing traditional SP3 mixed material for conventional mass spectrometry analysis of protein.

In order to achieve the objective of the present disclosure, the present disclosure adopts the following technical solutions.

A method for identifying proteins peptides by mass spectrometry is provided, including the following steps:

S1. adding a binding buffer and an aluminosilicate zeolite to a sample to be tested to obtain a first suspension;

S2. incubating the first suspension, subjecting an incubated first suspension to first high-speed centrifugation to obtain a first supernatant and a first precipitate, discarding the first supernatant, and retaining the first precipitate;

S3. repeating a process as follows several times: resuspending the first precipitate with a washing buffer to obtain a second suspension, subjecting the second suspension to second high-speed centrifugation to obtain a second supernatant and a second precipitate, discarding the second supernatant, and retaining the second precipitate; and S4. preparing the second precipitate into a protein sample, and subjecting the protein sample to mass spectrometry detection.

Preferably, in the S1, the sample to be tested is selected from a group consisting of purified proteins, protein groups, purified peptides, and peptide groups derived from different species, sites, and purification means, and is preferably a serum/plasma or tissue/cell sample; and the binding buffer comprises one component or a combination of two or more components selected from a group consisting of Tris, monopotassium phosphate, dipotassium phosphate, potassium phosphate, phosphoric acid, monosodium phosphate, disodium phosphate, sodium phosphate, potassium chloride, sodium chloride, citric acid, sodium citrate, barbituric acid, barbital sodium, sodium hydroxide, hydrochloric acid, formic acid, acetic acid, EDTA, SDS, NP-40, CHAPS, Tween, Triton, PEG, acetonitrile, and methanol, and is preferably a combined buffer of Tris and EDTA.

Preferably, in the S1, the aluminosilicate zeolite is one or a mixture of two or more selected from a group consisting of 3A-type (potassium type-A), 4A-type (sodium type-A), 5A-type (calcium type-A), 10Z-type (calcium type-Z), 13Z-type (sodium type-Z), Y-type (sodium type-Y), and sodium mordenite-type zeolites, or is a mixture of two or more selected from a group consisting of zeolites of a same type. Preferably, the aluminosilicate zeolite is a Y-type zeolite and is added at an amount of 0.01 mg/mL to 100 mg/mL. More preferably, the aluminosilicate zeolite is a mixture of Y-type zeolites HY, NaY, and LaY in a mass ratio of 1:(0.5-2):(0.5-2) and preferably 1:1:1.

Preferably, in the S2, the incubating is conducted at 18° C. to 37° C. for 1 min to 120 min.

Preferably, in the S2, the first high-speed centrifugation is conducted for 5 min to 120 min at a centrifugal force of 8,000 g to 22,000 g and a temperature of 2° C. to 8° C.

Preferably, in the S3, the washing buffer is selected from a group consisting of the binding buffer used in the S1 or a corresponding diluent.

Preferably, in the S3, the second high-speed centrifugation is conducted for 5 min to 120 min at a centrifugal force of 8,000 g to 22,000 g and a temperature of 2° C. to 8° C.; and the process is repeated several times and preferably three times.

Preferably, in the S4, the preparation of the protein sample includes preparation of a protein sample or preparation of a peptide sample:
  a preparation method of the protein sample includes the following steps:
  resuspending the second precipitate with a buffer of a reducing agent, and after a reaction, adding an alkylation reagent for alkylation of sulfhydryl; and adding sequencing-grade trypsin and a digestion buffer, and achieving enzymolysis and desalination to obtain the protein sample; and
  a preparation method of the peptide sample includes the following steps:
  resuspending the second precipitate with a desorption solution (preferably 2% acetonitrile) to obtain a third suspension, and ultrasonically-treating and centrifuging the third suspension to obtain a third supernatant, namely, the peptide sample.

Further preferably,
  the reducing agent is dithiothreitol or tris(2-carboxyethyl) phosphine; the alkylation agent is iodoacetamide or chloroacetamide; after the reducing agent is added, a first reaction is conducted at 45° C. to 95° C. for 0 min to 60 min, then the alkylation agent is added, and a second reaction is conducted at room temperature for 5 min to 60 min in dark;
  the digestion buffer includes calcium chloride and ammonium bicarbonate, and has a pH of 7.0 to 8.5; the trypsin is added at an amount of 0.1 ng/μL to 100 ng/μL; the enzymolysis is conducted at 25° C. to 37° C. for 1 h to 16 h; and the desalination includes the following steps: conducting adsorption with the aluminosilicate zeolite, an SDB column, a C18 column, or an SP3 magnetic bead, cleaning, and conducting desorption.

Preferably, in the S4, a method of the mass spectrometry detection includes:
  detecting by liquid chromatography-tandem mass spectrometry, and conducting extraction on obtained data with software to obtain qualitative and quantitative data of proteins and peptides.

The aluminosilicate zeolite is a synthetic hydrated aluminosilicate with a molecular screening effect. Its general chemical formula is (M'2M)O·Al2O3·xSiO2·yH2O, where M' and M represent monovalent and divalent cations, respectively, such as K+ or Na+ and Ca2+ or Ba2+. According to different molecular ratios of SiO2 to Al2O3, zeolites with different pore sizes are obtained. Models of the aluminosilicate zeolite include 3A-type (potassium type-A), 4A-type (sodium type-A), 5A-type (calcium type-A), 10Z-type (calcium type-Z), 13Z-type (sodium type-Z), Y-type (sodium type-Y), and sodium mordenite-type. A Y-type zeolite includes hydrogen, sodium, potassium, and calcium ions, and has a Y-type crystal structure, a silicon/aluminum ratio of 5 to 30, and a pore size of 1 nm to 10 nm. An aluminosilicate zeolite with merely a fixed parameter can be used alone, and a variety of aluminosilicate zeolites with different parameters can be used in combination.

Compared with the prior art, the present disclosure adopts an aluminosilicate zeolite and a corresponding binding buffer to effectively adsorb different protein and peptide samples. Thus especially for serum/plasma samples, low-abundance proteins and peptides in serum/plasma can be selectively enriched to effectively avoid the interference of high-abundance proteins on the identification of low-abundance proteins in serum/plasma during identification by mass spectrometry. The present disclosure can be used for identifying various proteins by mass spectrometry, and can achieve the qualitative and quantitative analysis of more than 2,000 serum/plasma proteins during single-run mass spectrometry analysis under a conventional chromatographic gradient. The method of the present disclosure involves simple operations, and only requires the four steps of incubation, centrifugation, elution, and centrifugation to complete the enrichment of low-abundance proteins and peptides in serum/plasma, improving the detection sensitivity and reduces a human operation error.

DETAILED DESCRIPTION OF THE EMBODIMENTS

The solutions of the present disclosure are comprehensively described below through examples, and the examples are the most preferred embodiments of the present disclosure. However, the present disclosure is not limited to the following examples.

Example 1

1. Different plasma samples of each of 200 μL were taken out from a refrigerator, thawed at 37° C., and then centrifuged at 1,500 g and 4° C. for 10 min to obtain a first precipitate at a bottom and a first supernatant, the first precipitate was removed, and the first supernatant was transferred to a fresh tube.

2. 100 μL of the first supernatant was taken, 100 μL of a Y-type mixed material (HY:NaY:LaY, 1:1:1, HY(NKF-8) silicon/aluminum ratio: 10, NaY(NKF-7) silicon/aluminum ratio: 4.8 to 5.4, and LaY(NKF-8-2) silicon/aluminum ratio: larger than or equal to 5.1) resuspended with a binding buffer (50 mM Tris and 10 mM EDTA) was added, and the resulting mixture was incubated at room temperature for 30 min.

3. A system produced after the incubation was centrifuged at 12,000 g for 10 min to obtain a second precipitate and a second supernatant, the second supernatant was removed, and the second precipitate was resuspended with 200 μL of the binding buffer; and the resulting suspension was centrifuged at 12,000 g for 5 min to obtain a third precipitate and a third supernatant, and the third supernatant was removed.

Figure 1:
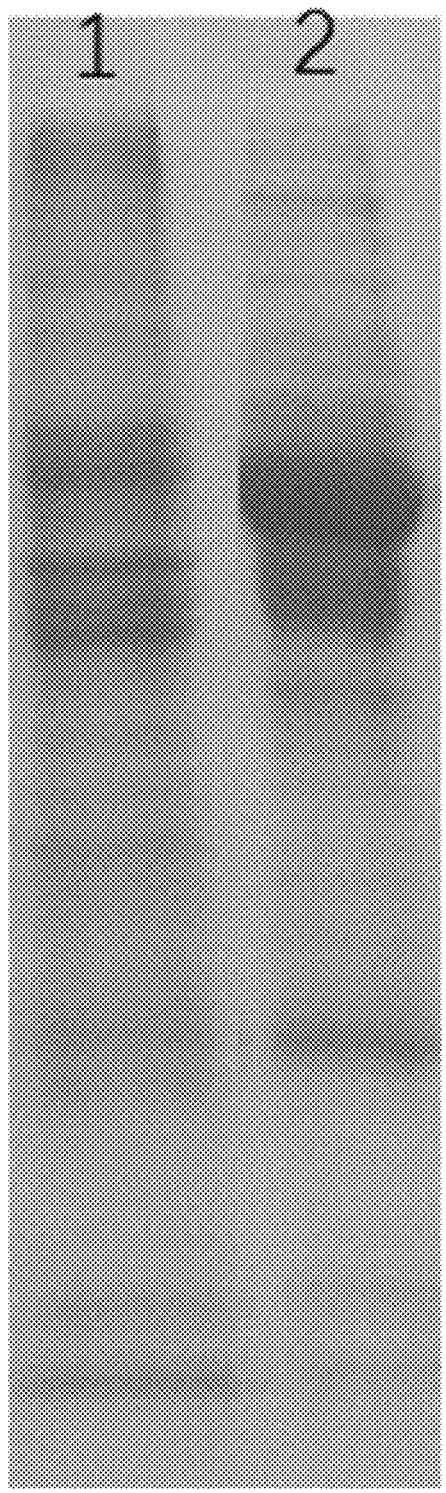
FIG. 1 shows protein electrophoresis results of the same plasma before and after adsorption with a Y-type material, where 1 shows protein electrophoresis results after adsorption with the Y-type material and 2 shows protein electrophoresis results of the original plasma.

4. The step 3 was repeated twice.
5. A final precipitate produced after the combination of the original plasma with the material was added to a protein electrophoresis loading buffer and boiled, and a resulting supernatant was subjected to electrophoresis. Electrophoresis results are shown in FIG. 1.
6. A precipitate that was prepared in parallel and did not undergo electrophoresis was resuspended with a specified volume of a DTT-containing buffer, and a first reaction was conducted at 95° C. for 1 h.
7. A specified volume of IAM was added, and a second reaction was conducted at room temperature for 45 min in the dark.
8. A digestion buffer and trypsin were added to obtain a first mixed system, and the first mixed system was thoroughly mixed and subjected to enzymolysis overnight at 37° C.
9. An excess amount of a formic acid solution was added to obtain a second mixed system, the second mixed system was centrifuged at 12,000 g for 10 min, and the resulting supernatant was added to an SDB desalination column and centrifuged, such that peptides produced after the enzymolysis bound to the SDB desalination column.
10. The SDB desalination column was washed several times and subjected to desorption to obtain a purified peptide solution.
11. The purified peptide solution was lyophilized and then re-dissolved with a loading buffer.
12. The resulting peptide suspension was tested by nanoliter high-performance liquid chromatography-tandem mass spectrometry for DIA data acquisition.
13. Extraction was conducted on mass spectrometry data with the Spectronaut software and the established serum/plasma database to obtain qualitative and quantitative results of proteins.
14. Four plasma samples from different sources were treated by three operators simultaneously, and three parallel replicates were set for each sample. Numbers of peptides and proteins identified are shown in Table 1:

TABLE 1

Identification results of plasma proteins by mass spectrometry

| SAMPLE | OPERATOR 1 | | OPERATOR 2 | | OPERATOR 3 | |
| --- | --- | --- | --- | --- | --- | --- |
|  | Peptides | Proteins | Peptides | Proteins | Peptides | Proteins |
| SAMPLE1-1 | 9923 | 2178 | 10363 | 2134 | 10388 | 2188 |
| SAMPLE1-2 | 10153 | 2207 | 10481 | 2048 | 9703 | 2096 |
| SAMPLE1-3 | 10097 | 2194 | 9393 | 2048 | 10484 | 2150 |
| SAMPLE2-1 | 10339 | 2016 | 10150 | 2008 | 9272 | 2018 |
| SAMPLE2-2 | 10995 | 2066 | 10322 | 2063 | 9796 | 2065 |
| SAMPLE2-3 | 9530 | 2102 | 9024 | 2018 | 10938 | 2188 |
| SAMPLE3-1 | 10965 | 2038 | 9559 | 2157 | 9163 | 2002 |
| SAMPLE3-2 | 10987 | 2132 | 9495 | 2016 | 10172 | 2053 |
| SAMPLE3-3 | 9825 | 2033 | 9093 | 2112 | 9603 | 2161 |
| SAMPLE4-1 | 9007 | 2197 | 10454 | 2041 | 10226 | 2070 |
| SAMPLE4-2 | 10132 | 2035 | 9877 | 2076 | 9679 | 2170 |
| SAMPLE4-3 | 10010 | 2080 | 9511 | 2047 | 9374 | 2188 |

15. Identification results when high-abundance proteins were depleted from plasma with the Y-type zeolite were compared with identification results when plasma was directly subjected to enzymolysis without any treatment and identification results when high-abundance proteins were depleted from plasma with an antibody-based high-abundance protein-depletion kit. Comparison results are shown in Table 2:

TABLE 2

Numbers of proteins and peptides identified when a treatment is conducted with a Y-type zeolite, when direct enzymolysis is adopted, and when a treatment is conducted with the antibody-based high-abundance protein-depletion kit

| SAMPLE | ZEOLITE GROUP | | ORIGINAL SAMPLE CONTROL | | ANTIBODY-BASED HIGH-ABUNDANCE PROTEIN-DEPLETION GROUP | |
| --- | --- | --- | --- | --- | --- | --- |
|  | Peptides | Proteins | Peptides | Proteins | Peptides | Proteins |
| SAMPLE1-1 | 9923 | 2178 | 2181 | 375 | 3694 | 678 |
| SAMPLE1-2 | 10153 | 2207 | 2241 | 324 | 3352 | 696 |
| SAMPLE1-3 | 10097 | 2194 | 1697 | 324 | 3742 | 648 |
| SAMPLE2-1 | 10339 | 2016 | 2075 | 304 | 3136 | 618 |
| SAMPLE2-2 | 10995 | 2066 | 2161 | 332 | 3398 | 665 |
| SAMPLE2-3 | 9530 | 2102 | 1512 | 309 | 3969 | 788 |
| SAMPLE3-1 | 10965 | 2038 | 1780 | 378 | 3082 | 602 |
| SAMPLE3-2 | 10987 | 2132 | 1747 | 308 | 3586 | 653 |
| SAMPLE3-3 | 9825 | 2033 | 1546 | 356 | 3302 | 761 |
| SAMPLE4-1 | 9007 | 2197 | 2227 | 321 | 3613 | 670 |
| SAMPLE4-2 | 10132 | 2035 | 1938 | 338 | 3340 | 770 |
| SAMPLE4-3 | 10010 | 2080 | 1756 | 323 | 3187 | 788 |

Figure 2:
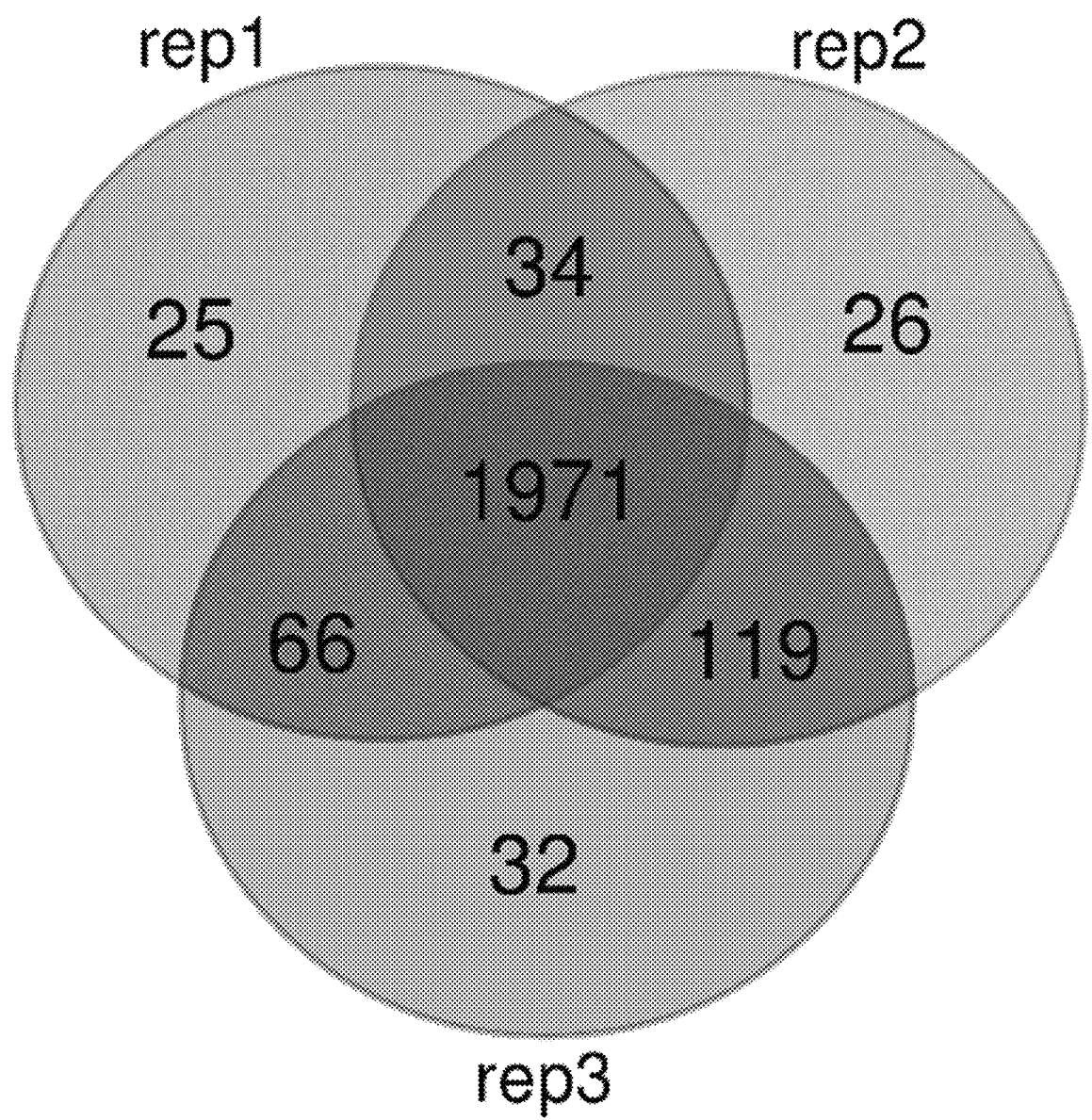
FIG. 2 is a Venn diagram of protein co-identification results of a same sample after undergoing three replicate treatments with a Y-type zeolite.
Figure 3:
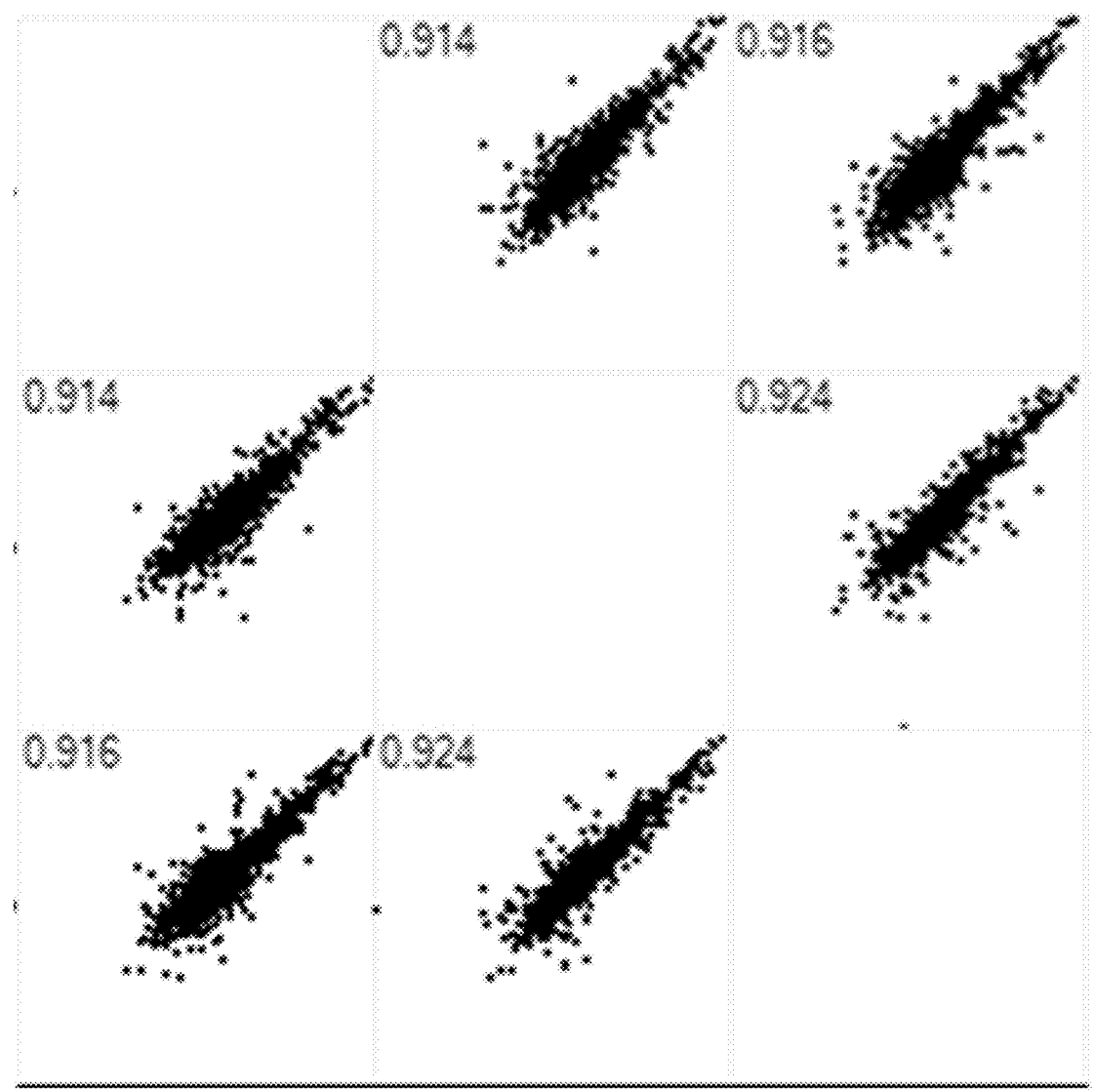
FIG. 3 shows the correlation of protein-quantification data of a same sample after undergoing three replicate treatments with a Y-type zeolite.

16. With SAMPLE1 as an example, co-identification analysis is conducted on proteins identified in three replicates provided by the operator 3. Numbers of co-identified proteins are shown in FIG. 2, and the correlation of protein quantification data is shown in FIG. 3.

Conclusion:

1. It can be seen from FIG. 1 that the zeolite can well deplete high-abundance proteins.
2. It can be seen from Table 1 that there is a high degree of similarity among a plurality of replicates of each sample, numbers of proteins identified in plasma samples from different sources are also similar, and different operators have similar operation results. Therefore, in each replicate, more than 2,000 proteins and about 10,000 peptides are identified. Therefore, the zeolite method is stable.
3. Only 300+ proteins and about 2,000 peptides are identified in an untreated plasma sample, and 3,000 to 4,000 peptides and 600 to 800 proteins are identified in a plasma sample treated with the antibody-based high-abundance protein-depletion, which all are much smaller than the results of the Y-type zeolite group.
4. The co-identification analysis of proteins and the correlation analysis of protein quantification data indicate that protein enrichment results of the zeolite for a single sample are very stable and highly reproducible.

Example 2

In order to demonstrate that the zeolite can achieve the enrichment, enzymolysis, and desalination of microsamples at a protein level or a peptide level and can be used as an alternative for the existing traditional SP3 hybrid magnetic bead material, in this example, protein and peptide extracts of Hela cells were subjected to a proteomics analysis experiment with an SP3 hybrid material as a control group and the Y-type material in Example 1 as a carrier.

With a protein standard extracted from Hela cells as an example:

1. Two Hela cell protein samples each with 100 μg of Hela cell proteins dissolved in 40 μL of a buffer (4% SDS, 100 mM Tris, pH 8.0) were taken and subjected to a reductive alkylation reaction.
2. 10 μL of a stored 10 μg/μL SP3 hybrid bead and an equal amount of a Y-type zeolite material (HY:NaY:LaY: 1:1:1, HY(NKF-8) silicon/aluminum ratio: 10, NaY(NKF-7) silicon/aluminum ratio: 4.8 to 5.4, and LaY(NKF-8-2) silicon/aluminum ratio: larger than or equal to 5.1) were added respectively into the two Hela cell protein samples, then 150 μL of a buffer and 200 μL of acetonitrile were added as a binding buffer, and after thorough mixing by gently shaking, reactions were conducted at room temperature for 8 min.
3. The two resulting reaction systems were each centrifuged by a centrifuge at 12,000 g for 5 min to each obtain a first precipitate and a first supernatant, the first supernatant was gently discarded without contacting the bead or the material, and then 200 μL of 70% ethanol was added to each of the systems to obtain mixtures; and the mixtures were each gently shaken for thorough mixing and then centrifuged at 12,000 g for 5 min to each obtain a second precipitate and a second supernatant, and the second supernatant was gently discarded. This step was repeated.
4. 180 μL of 100% acetonitrile was added, and after thorough mixing by gently shaking and instantaneous centrifugation to obtain a third precipitate and a third supernatant, the third supernatant was gently discarded, and the third precipitate was naturally dried for 30 s.
5. Appropriate amounts of a digestion buffer and trypsin were added, and after enzymolysis overnight at 37° C., a peptide product (A) of (SP3+enzymolysis) and a peptide product (B) of (Y-type material+enzymolysis) were obtained.
6. The Y-type material was added to the peptide product (A) of (SP3+enzymolysis) to obtain a mixture, and the mixture was gently pipetted up and down for thorough mixing of the beads and the Y-type material; acetonitrile was added at a final concentration of at least 95% as a binding buffer to obtain a mixture, and the mixture was gently shaken for thorough mixing, incubated at room temperature for 5 min, and centrifuged at 12,000 g for 5 min to obtain a fourth precipitate and a fourth supernatant, and the fourth supernatant was gently discarded without contacting the bead or the material; 180 μL of acetonitrile was added to obtain a mixture, the mixture was gently shaken for thorough mixing and then instantaneously centrifuged to obtain a fifth precipitate and a fifth supernatant, and the fifth supernatant was gently discarded; an appropriate volume of 2% acetonitrile was added to obtain a mixture, the mixture was instantaneously centrifuged for 2 s, the bead or the material on a tube wall was gently pushed into a solution by a pipette tip, and the solution was gently shaken for thorough mixing, ultrasonically treated for 30 s, and then instantaneously centrifuged for 2 s to obtain a sixth supernatant; and the sixth supernatant was gently transferred to a new centrifuge tube and centrifuged at 12,000 g for 5 min to obtain a seventh supernatant, and the seventh supernatant was gently collected to obtain a peptide product (C) of (SP3+ enzymolysis+desalination).
7. The Y-type material was added to each of the peptide product (A) (SP3+enzymolysis), the peptide product (B) (Y-type material+enzymolysis), and 100 μg of the peptide product (C) (SP3+enzymolysis+desalination) to obtain three mixtures, and the three mixtures were gently pipetted up and down for thorough mixing; acetonitrile was respectively added at a final concentration of at least 95% as a binding buffer, and the mixtures were gently shaken for thorough mixing, incubated at room temperature for 5 min, and centrifuged at 12,000 g for 5 min to each obtain an eighth precipitate and an eighth supernatant, and the eighth supernatant was gently discarded without contacting the bead or the material; and 180 μL of acetonitrile was added, the resultants were gently shaken for thorough mixing and then instantaneously centrifuged to each obtain a ninth precipitate and a ninth supernatant, and the ninth supernatant was gently discarded.
8. An appropriate volume of 2% acetonitrile was added to obtain mixtures, the mixtures were instantaneously centrifuged for 2 s, the bead or the material on a tube wall was gently pushed into solutions by a pipette tip, and the solutions were gently shaken for thorough mixing, ultrasonically treated for 30 s, and then instantaneously centrifuged for 2 s to each obtain a tenth supernatant; and the tenth supernatant was each gently transferred to a new centrifuge tube and centrifuged at 12,000 g for 5 min to obtain an eleventh supernatant, and the eleventh supernatant was gently collected into a sample bottle and tested on a machine.
9. The eleventh supernatant was each tested by nanoliter high-performance liquid chromatography-tandem mass spectrometry for DDA data acquisition.
10. Extraction was conducted on mass spectrometry data with the Maxquant software to obtain qualitative and quantitative results. The qualitative and quantitative results are shown in Table 3:

TABLE 3

Mass spectrometry detection results after enrichment with the Y-type material and the SP3 hybrid material at protein and peptide levels

| SAMPLE NO. | IDENTIFICATION RESULTS BY MASS SPECTROMETRY | |
| --- | --- | --- |
| | Number of peptides | Number of proteins |
| (A) TRADITIONAL SP3 HYBRID MATERIAL | 21336 | 4651 |
| (B) Y-TYPE MATERIAL_PROTEIN ENRICHMENT | 20529 | 4553 |
| (C) Y-TYPE MATERIAL_PEPTIDE ENRICHMENT | 18314 | 4371 |

CONCLUSION

It can be seen from the comparison of mass spectrometry detection results of the HeLa standard undergoing enrichment with the SP3 hybrid magnetic bead material and the Y-type zeolite material at protein and peptide levels that the Y-type material alone can be used instead of the traditional amino and carboxyl-modified SP3 hybrid material in a conventional mass spectrometry analysis method of protein for enrichment at protein and peptide levels.

What is claimed is:

1. A method for increasing a number of proteins identified by mass spectrometry, comprising the following steps:
   S1. adding a binding buffer and an aluminosilicate zeolite to a plasma sample to obtain a first suspension, wherein the aluminosilicate zeolite is a mixture of Y-type zeolites HY, NaY, and LaY in a mass ratio of 1:1:1;
   S2. incubating the first suspension, subjecting an incubated first suspension to first high-speed centrifugation to obtain a first supernatant and a first precipitate, discarding the first supernatant, and retaining the first precipitate;
   S3. repeating a process as follows several times: resuspending the first precipitate with a washing buffer to obtain a second suspension, subjecting the second suspension to second high-speed centrifugation to obtain a second supernatant and a second precipitate, discarding the second supernatant, and retaining the second precipitate, wherein the washing buffer is the binding buffer used in the S1;
   S4. preparing the second precipitate into a protein sample, and subjecting the protein sample to mass spectrometry detection; and
   S5. identifying more than 2,000 proteins in the treated plasma sample, wherein the binding buffer comprises one component or a combination of two or more components selected from a group consisting of Tris, dipotassium phosphate, potassium phosphate, phosphoric acid, monosodium phosphate, sodium phosphate, citric acid, sodium citrate, barbituric acid, barbital sodium, sodium hydroxide, hydrochloric acid, formic acid, acetic acid, EDTA, SDS, NP-40, Tween, Triton, PEG, acetonitrile, and methanol.

2. The method for increasing the number of proteins identified by the mass spectrometry according to claim 1, wherein in the S2, the incubating is conducted at 18° C. to 37° C. for 1 min to 120 min; and the first high-speed centrifugation is conducted for 5 min to 120 min at a centrifugal force of 8,000 g to 22,000 g and a temperature of 2° C. to 8° C.

3. The method for increasing the number of proteins identified by the mass spectrometry according to claim 1, wherein in the S3, the second high-speed centrifugation is conducted for 5 min to 120 min at a centrifugal force of 8,000 g to 22,000 g and a temperature of 2° C. to 8° C.; and the process is repeated three times.

4. The method for increasing the number of proteins identified by the mass spectrometry according to claim 1, wherein in the S4,
   a preparation method of the protein sample comprises the following steps:
   resuspending the second precipitate with a buffer of a reducing agent, and after a reaction, adding an alkylation reagent for alkylation of sulfhydryl; and
   adding sequencing-grade trypsin and a digestion buffer, and achieving enzymolysis and desalination to obtain the protein sample.

5. The method for increasing the number of proteins identified by the mass spectrometry according to claim 4, wherein the reducing agent is dithiothreitol or tris(2-carboxyethyl)phosphine; the alkylation agent is iodoacetamide or chloroacetamide; after the reducing agent is added, a first reaction is conducted at 45° C. to 95° C. for 0 min to 60 min, then the alkylation agent is added, and a second reaction is conducted at room temperature for 5 min to 60 min in dark;
   the digestion buffer comprises calcium chloride and ammonium bicarbonate, and has a pH of 7.0 to 8.5; the trypsin is added at an amount of 0.1 ng/µL to 100 ng/µL; the enzymolysis is conducted at 25° C. to 37° C. for 1 h to 16 h; and the desalination comprises the following steps: conducting adsorption with the aluminosilicate zeolite, an SDB column, a C18 column, or an SP3 magnetic bead, cleaning, and conducting desorption.

6. The method for increasing the number of proteins identified by the mass spectrometry according to claim 1, wherein in the S4, a method of the mass spectrometry detection comprises:
   detecting by liquid chromatography-tandem mass spectrometry, and conducting extraction on obtained data with software to obtain qualitative and quantitative data of proteins and peptides.

* * * * *